United States Patent [19]

Deguchi

[11] Patent Number: 4,985,466
[45] Date of Patent: Jan. 15, 1991

[54] METHOD FOR TREATING TUMORS SUSCEPTIBLE TO TREATMENT WITH REDUCED WOOL ALCOHOL

[75] Inventor: Hisashi Deguchi, Miyoshi, Japan

[73] Assignee: Dai-Ichi Kogyo Seiyaku Co., Ltd., Kyoto, Japan

[21] Appl. No.: 206,446

[22] Filed: Jun. 14, 1988

[51] Int. Cl.$^5$ .................. A61K 31/045; A61K 35/12; A61K 35/36
[52] U.S. Cl. ...................................... 514/724; 514/739
[58] Field of Search ................... 514/724, 739; 424/95

[56] References Cited

PUBLICATIONS

Chemical Abstracts 83:117589d (1975).
Dyer, An Index of Tumor Chemotherapy, NIH, Mar. 1949, pp. 10–12 and 132.
Miwa et al, Anticancer Research 6, 1033–1036 (1986).

Primary Examiner—Jerome D. Goldberg
Attorney, Agent, or Firm—Armstrong, Nikaido, Marmelstein, Kubovcik & Murray

[57] ABSTRACT

Tumors in an animal having a tumor susceptible to such treatment are treated by administering to the animal an effective amount of a wool fatty acid, wool fatty alcohol or wool fatty acid derivative.

1 Claim, No Drawings

METHOD FOR TREATING TUMORS SUSCEPTIBLE TO TREATMENT WITH REDUCED WOOL ALCOHOL

BACKGROUND OF THE INVENTION

The present invention relates to a method for treating tumors susceptible to treatment with a wool fatty acid, a wool alcohol, their particular components, or derivatives thereof.

SUMMARY OF THE INVENTION

In accordance with the present invention, there is provided a method for the treatment of tumors susceptible to treatment with a wool fatty acid, a reduced alcohol derived from wool fatty acid, a metal salt of wool fatty acid, a wool fatty acid ester, a wool alcohol, a carboxylic acid derived from a wool alcohol, a wool alcohol ether and a wool alcohol ester.

DETAILED DESCRIPTION

In the present invention, the term "wool fatty acid" means an acidic component of a wool grease, which is a wool oil. The term "wool alcohol" in the present invention means an alcoholic component of a wool grease.

A wool fatty acid and a wool alcohol are prepared by the separation from the hydrolysis product of a wool grease. For instance, a wool grease or a concentrated waste fluid after washing wool is dissolved in acetone, and thereto three-fold equivalent of calcium oxide necessary for saponification of wool greese are added. When the mixture is reacted at 150° C. under 5 atmospheres for 8 hours, an acidic component is precipitated as a calcium salt. On the other hand, from the same mixture, under atmospheric pressure at 55° C., a wool alcohol is extracted, since an alcohol component is soluble in acetone under this condition. Then three-fold volume of acetone and 0.2-fold volume of sulfuric acid versus calcium oxide are added to the above-obtained calcium salt of acidic component. The mixture is reacted at 60° C. for 2 hours to subject the calcium salt to acid decomposition. After filtration, acetone in the filatrate is evaporated and the resultant is wahsed with water to give a wool fatty acid as a solid.

A wool fatty acid is present as a mixture of not less than 60 kinds of a carboxylic acid having 10 to 31 carbon atoms, for instance, an iso, anteiso, $\alpha$-hydroxy or straight-chain higher saturated fatty acids, resin acids, and the like. A wool alcohol contains iso, anteiso or straight-chain higher saturated aliphatic alcohols having 16 to 30 carbon atoms, sterols such as choresterol, tri-terpene alcohols such as lanosterol, hydrocarbons, and the like. A wool alcohol is present as a mixture of not less than 30 kinds of the compounds. It is characteristic of a wool fatty acid and of a wool alcohol to contain a large quantity of iso and anteiso higher saturated aliphatic compounds.

A particular component of wool fatty acid or wool alcohol, which contains branched saturated aliphatic compounds having 11 to 17 carbon atoms is prepared, for example, by molecular distillation. For instance, distillates of a wool fatty acid and a wool alcohol, in high vacuo below $10^{-4}$ mmHg with semi-micro pot still, the molecular distillation temperature of which are 75° C. to 110° C. and 60° C. to 95° C. respectively are especially effective. It is preferable to purify them by urea clathrate method. That is, each distillate is dissolved in methanol. Urea is added thereto and is dissolved with warming. Then the solution is allowed to stand with cooling to precipitate crystals. After filtration, hydrochloric acid is poured upon the filtrate. The mixture is extracted with hexane and ether alternately, washed with water, and then dried over mirabilite. The products are obtained by distilling away the solvent. According to gas chromatography (Chromosorb w/15%ECSS-X/178° C.) and to infrared spectrum analysis with KBr tablet, both of the products contain as main components iso and anteiso branched saturated aliphatic monocarboxylic acids and monohydric alcohols having 11 to 17 carbon atoms. They are iso and anteiso undecylic acid, iso and anteiso lauric acid, iso and anteiso tridecylic acid, iso and anteiso myristic acid, iso and anteiso pentadecylic acid, iso and anteiso palmitic acid, iso and anteiso margaric acid and corresponding alcohols thereto.

The term "wool fatty acid derivative" in the present invention means the following 3 kinds:

(1) A reduced alcohol: A wool fatty acid is reduced with hydrogenated aliminium lithium to convert a carboxyl group into methylol group.

(2) A metal salt: A saturated aqueous solution of a copper or iron salt is mixed with twice moles of a saturated acetone solution of a wool fatty acid, and the mixture is sprayed and dried to give a copper salt or iron salt of wool fatty acid. A wool fatty acid is reacted with a carbonate or hydrogen carbonate of alkaline metals such as sodium and pottasium to give an alkaline metal salt of wool fatty acid. A calcium salt is prepared in the process of the above-mentioned process for preparing a wool fatty acid. Also, magnesium, zinc, cobalt or selenium salts are included.

(3) An ester: A wool fatty acid is subjected to Fischer Esterificaiton with a lower saturated aliphatic alcohol such as methyl, ethyl, propyl, isopropyl or butyl alcohol, ethylene glycol, glycerin, ascorbic acid, sucrose, or the like.

The term "wool alcohol derivative" in the present invention means the following 3 kinds:

(1) A carboxylic acid: A chloride of wool alcohol is obtained with using phosphorus pentaoxide. The choloride is dissolved in dry ether and magnesium is added thereto to obtain the Grignard compound. Then the obtained compound is reacted with dried carbon dioxide at a low temperature, to obtain a carboxylic acid by reduction with hydrogen.

(2) An ether: It is obtained by means of Williamson Synthesis of ether with using a chloride of wool alcohol and a lower saturated aliphatic sodium alkoxide. Also, ethylene glycol monoether is obtained by reacting ethylene oxide and a wool alcohol in the presence of sulfuric acid.

(3) An ester: It is prepared by reacting an acid anhydride of lower fatty acid such as acetic acid, propionic acid or butyric acid and a wool alcohol in the presence of sulfuric acid.

The aforesaid wool fatty acid wool fatty alcohols or wool fatty acid derivatives can be used in any dosage forms for injection, instillation, oral administration, and the like. For instance, for injection or instillation, they are formulated in the following manner. That is, a surface active agent such as Pluronic F68 (Asahi Denka Co., Tokyo) or HCO-60 (Nikko Chemicals Co., LTD.) is added to the active ingredient, and it is dispersed by ultrasonic or it is made to form a liposome or an oil in water emulsion. And thereto may be added antiseptics such as p-hydroxybenzoic acid methyl ester, stabilizers such a lecithin, linoleic acid, non aqueous vehicle such as coconuts oil, suspending agents such a glucose. For oral administration, capsules suitable for intestinal absorption are formulated with adhesives such as gelatin, stabilizers such as magnesium stearate, excipients such a lactose, disintegrators such as potato starch and an enteric coating is formed with cellulose acetate phthalate, copolymer of methyl acrylate and methacrylic acid, and the like. The active ingredient can be also formulated in the form of a granule, a sustained release buried capsule, a suppositoria, a nebulizer and a buccal.

The ratio of the active ingredient to the vehicle or excipient in a dorsage form can vary from $10^{-6}$ to $10^2$ (weight/weight).

It is preferable to adminster the wool fatty acid, wool fatty alcohol or wool fatty acid derivative in doses of the active ingredient of 10 to 1500 mg especially 50 to 500 mg/day/1kg body weight to an adult by non oral administration such as intravenous injection, subcutaneous injection or instillation. By oral administration, for example in capsules, is 0.2 to 50 g expecially 1 to 10 g of the active ingredient is preferable. The $LD_{50}$ value of toxicity for the hypodermically injected rat is 3.4 g/kg and a side effect can not be found with continuous administration for 10 days in does of 800 mg/kg.

The present invention is more particularly described and explained by the following Examples. However, it should be understood that the present invention is not limited to such Examples and various changes and modifications can be made without departing from the scope and spirit of the present invention.

EXAMPLE 1

On a celiac of ddy strain mouse the age of which was 5 weeks, $10^6$ cells of Ehrlich ascites carcinoma were inoculated. After 24 hours, to groups of 10 mice each, each sample suspended in a solution of 0.25% Pluronic F68 and a physiological saline at a concentration of 50 mg/ml was intraperitoneally injected in doses of 400 mg/Kg/day for 10 days. While the control group to which the same solution not containing the sample was administered was survived for 13.4 days from the inoculation (the day of inoculation was counted as 0 day and the next day was counted as first day) on the average, the administered group of a wool grease was survived for 24.2 days, the administrated group of a wool fatty acid was survived for 28.0 days, the administreated group of a wool alcohol was survived for 32.5 days. Thus a significant increase in life-span was found.

EXAMPLE 2

To a dorsum of first filial generation mouse of C57BL/6 and DBA/2 strains which were 6 weeks of age, $10^6$ cells of adeno carcinoma 755 were implanted hypodermically. After 24 hours to groups of 10 mice, each sample suspended in a solution of 0.25% HCO-60 (a detergent from Nikko Chem. Co., Tokyo) and a physiological saline at a concentration of 50 mg/ml, was subcutaneously injected in doses of 300 mg/Kg/day for 7 days. The tumor was weighed after 25 days from the implantation. While the average weight of tumor was 6.4 g in the control group, the average weight of tumor was 4.8 g in the group to which a wool fatty acid was administrated, 5.0 g in the group of a wool alcohol, 3.7 g and 4.1 g in the groups of the distillates of molecular distillation of wool fatty acid at a temperature of 75° C. to 110° C. and of wool alcohol at a temperature of 60 ° C. to 95° C. respectively, and 2.4 g and 2.6 g respectively in the groups of the branched saturated aliphatic components which were purified from the above distillates by the urea inclusion body method. Thus a siginificant tumor inhibiting effect of the wool fatty acid, wool fatty alcohol or wool fatty acid derivative was found.

EXAMPLE 3

To an inguen of Wistar rat the age of which was 6 weeks, $10^4$ cells of Walker carcinoma 256 were implanted hypodermically. After 24 hours, to groups of 10 rats each was intraperitoneally administered each sample suspended in a solution of 0.25% HCO-60 and phsiological saline at a concentration of 30 mg/ml in doses of 100 mg/Kg/day for 10 days. The average tumour size ($mm^2$) after 20 days from the implantation (the day of implanation is counted as 0 day and the next day is counted as first day) was 447 in the control group, 134 for the group to which a wool fatty acid was administered, 123, 103, 116, 65 and 82, in a reduced alcohol of wool fatty acid, a methyl ester of wool fatty acid, a sucrose ester of wool fatty acid, a ferrous sulfate salt of wool fatty acid, a cupric chloride salt of wool fatty acid respectively, and 147, 120, 96, 70 and 64 for a wool alcohol, a carboxylic acid derived from wool alcohol, an acetic ester of wool alcohol, a methyl ether of wool alcohol, an ethylene glycol monoehter of wool alcohol respectively. Thus a significant tumor inhibiting effect of the wool fatty acid, wool fatty alcohol or wool fatty acid derivative was found.

PREPARATION EXAMPLE 1

Two fractions containing a branched saturated aliphatic compounds which were prepared by purifying the distillates of molecular distillation of a wool fatty acid at 75° C. to 110° C. and of molecular distillation of a wool alcohol at 60° C. to 95° C., by the urea clathrate method, were analysed by the infrared spectrum analysis with KBr tablet and a CaF prism at a high or a low concentration of the sample. There was no absorption band of a saturated straight-chain aliphatic group or an alken. There was observed 1379 $cm^{-1}$ of a branched fatty acid and 2870 $cm^{-1}$ of an alkan. These fractions were analysed by gas chromatography (Chromosorb/1-5% ECCS-Y/178° C.). Each standard compound was prepared by increasing succesively the carbon number of diazoketon, which was prepared by reacting diazomethane and isovaleric acid or sec-butyric acid in ether, by the Arndt-Eistert Synthesis with using alcohol in the presence of AG catalyst. As a result of this analysis, iso($\omega$1-methyl) and anteiso($\omega$2-methyl) saturated aliphatic monocarboxylic acids having 11 to 17 carbon atoms and the corresponding monohydric alcohols were identified.

EXAMPLE 4

Among the components prepared by Preparation Example 1, iso-pentadecylic acid (13-methyl-1-tetradecanoic acid) and anteiso tridecyl alcohol (10-methyl-1-dodecanol) lowered the cloning efficiency of human cervix carcinoma Hela S3 cells in Eagle's MEM-10% calf serum to $6.2 \times 10^{-3}$ and $9.4 \times 10^{-3}$ respectively by treatment for 6 hours at a concentration of 15 $\mu$M as compared with the untreated cells.

In addition to the ingredients used in the Examples, other ingredients can be used in the Examples as set forth in the specification to obtain substantially the same results.

What I claim is:

1. A method for treating a tumor in an animal having a tumor susceptible to such treatment, which comprises administering to the animal an anti-tumor composition containing, as an active ingredient, an anti-tumor effective amount of a reduced alcohol derived from wool fatty acid or a wool alcohol, said alcohol consisting of branched saturated aliphatic monohydric alcohols having 11 to 17 carbon atoms, and a pharmaceutically acceptable carrier, wherein the weight/weight ratio of the wool alcohol to the carrier is $10^{-6}$ to $10^2$.

* * * * *